United States Patent [19]

Heckmann

[11] Patent Number: 5,000,919
[45] Date of Patent: Mar. 19, 1991

[54] TESTING TUBE CONSTRUCTION FOR TESTING GASES WHICH ARE DISSOLVED IN LIQUIDS AND A METHOD OF MAKING THE SAME

[75] Inventor: Johannes Heckmann, Lubeck, Fed. Rep. of Germany

[73] Assignee: Drägerwerk A.G., Lubeck, Fed. Rep. of Germany

[21] Appl. No.: 250,707

[22] Filed: Sep. 28, 1988

[30] Foreign Application Priority Data

Dec. 9, 1987 [DE] Fed. Rep. of Germany ....... 3741664

[51] Int. Cl.$^5$ ............................................. G01N 21/78
[52] U.S. Cl. ...................................... 422/58; 422/59; 422/82.05; 422/86; 422/88; 427/2; 427/296; 436/68; 436/165; 436/178
[58] Field of Search ................. 436/166, 68, 165, 178; 422/58, 59, 83, 86, 88, 82.05; 427/2, 296

[56] References Cited

U.S. PATENT DOCUMENTS

| 2,929,687 | 3/1960 | Buchoff | 422/58 |
| 4,071,319 | 1/1978 | Nugent | 422/86 |
| 4,275,031 | 6/1981 | Fischer et al. | 422/58 |
| 4,325,890 | 2/1982 | Tamers | 422/58 |
| 4,557,902 | 12/1985 | Mussman | 422/59 |
| 4,790,857 | 12/1988 | Miksch | 422/86 |

FOREIGN PATENT DOCUMENTS

| 1157355 | 11/1983 | Canada | 150/21 |
| 2170599 | 8/1986 | United Kingdom | 422/86 |

OTHER PUBLICATIONS

Hackh's Chemical Dictionary, 4th edition, McGraw-Hill, Inc. 1969, p. 611.
The Merck Index, 10th Edition, Merck & Co., Inc.: Rahway, N.J., 1983, pp. 1220-1221.

Primary Examiner—Robert J. Hill, Jr.
Attorney, Agent, or Firm—McGlew & Tuttle

[57] ABSTRACT

A colorimetric test tube having a colorimetric indication which includes a simple detection system for testing gases dissolved in liquids. The test tube has an indicator for the colorimetric indication of gaseous substances to be detected and it has an opening covered against the environment to be tested with a hydrophobic membrane which is permeable to the substances whose presence is to be detected and which can be used for indicating the presence of gases dissolved in liquids. The membrane is advantageously sealed with a covering which dissolves upon immersion of the test tube in a liquid.

10 Claims, 1 Drawing Sheet

TESTING TUBE CONSTRUCTION FOR TESTING GASES WHICH ARE DISSOLVED IN LIQUIDS AND A METHOD OF MAKING THE SAME

BACKGROUND OF THE INVENTION

1. Field of the Invention

The invention relates, in general, to gas and other material for testing devices and, in particular, to a new and useful test tube with an indicator for the colorimetric indication of substances to be detected which has an opening that is closed against the environment with a hydrophobic membrane permeable to the substances to be detected.

A similar test tube has become known from Canadian Patent No. 1,157,355.

The known test tube has an opening that is closed with a permeable membrane through which harmful gaseous substances reach from the atmosphere to an indicator and there lead to coloration. By selecting suitable membrane materials, for example silicon rubber, a deliberate selectivity for the harmful gaseous substance to be detected is achieved.

The known test tube is used for demonstrating the presence of gaseous harmful substances in the ambient air. The increasing pollution of water with water-soluble harmful substances, however, also requires that water be monitored. For measuring chemical pollution in samples of water, according to DE-Z, Dragerheft 325, pages 18 to 20 (1983), an appropriate suitable test tube is connected to a washing bottle in which is contained the test sample of water. With a connected gas detector pump, air is pumped through the washing bottle which absorbs the harmful substance to be detected and carries it through the test tube. Carrying out such measuring method is cumbersome and requires several pieces of apparatus adjusted to each other such as washing bottle, test tube, and transporting pump.

SUMMARY OF THE INVENTION

The present invention provides a simple detection system on the basis of colorimetric indication for testing gases and liquids also.

Solution of the problem is achieved by using the indicator-containing test tube for indicating the presence of gases dissolved in liquids.

It has been shown that to demonstrate the presence of harmful gas dissolved in liquid, membranes of suitable permeability for the measurement in the liquid phase are available. Thus, many gaseous harmful substances which are soluble in water or in another liquid are accessible to colorimetric detection.

Since during measurement of the liquid containing dissolved gas, the test device is only intended to react with the substance to be detected (i.e., the gas), it is necessary to prevent other possibly harmful substances from permeating through the membrane into the test tube during the stand-by time or when operation of the device is begun in air (i.e., before its immersion in liquid). These harmful substances may give rise to unintentional coloration, and, hence, to falsification of the subsequent indication. This problem is avoided according to the invention by sealing the membrane with a coating solution in liquid form so that during its exposure to air, the indicator contained in the test tube remains unaffected. As soon, however, as it is immersed in a liquid in which the coating is soluble, the coating dissolves and the gas to be detected which is soluble in the liquid permeates through the membrane. The liquid dissolving the coating, here, can preferentially be the liquid itself which is to be tested, or it is another suitable solvent in which the membrane is placed before immersion into the liquid to be tested.

It is best if the coating comprises an organic or inorganic salt. Particularly advantageous for this purpose is lithium chloride (LiCl) but a coating of copper sulfate is also very suitable.

The coating closes the pores of the membrane and thus prevents gaseous harmful substances from coming into contact with the indicator. Only after the coating is removed by the solvent or the liquid to be tested itself (for example water) is the salt dissolved and the pores of the membrane washed free.

A particularly advantageous design of the test tube is given in that, at the end opposite to the opening provided with the membrane, an air-filled chamber is provided in its interior. In this way, it is achieved that when the sample is taken in the liquid test, the tube remains always immersed in the liquid like a buoy. This increases the reliability of the sampling.

A good method for producing a coating for sealing the membrane comprises wetting the membrane with a hot-saturated solution of the salt provided for sealing in water with the addition of a wetting agent in excess and, subsequently, evaporating the solvent. This process can, if necessary, be repeated several times. Through the high content of a wetting agent, for example ethyl alcohol, the hydrophobic property of the membrane material is cancelled so that the solution can wet the membrane and the dissolved salts can penetrate into the pores of the membrane. After the solvent has evaporated, the dissolved salts crystallize out and in this way occlude the membrane pores. Only when, subsequently, the test tube sealed in this manner, is immersed for testing; for example in water, are the salt crystals washed out of the pores and these are opened again.

Suitable membrane materials are polyethylene, polytetrafluoroethylene (PTFE), Polyvinylidenefluoride (PVDE), polyvinylchloride, polypropylene or their copolymers. Suitable coatings are, apart from copper sulfate, also sodium chloride and sodium sulfate. Suitable organic salts are saccharide, which also have high alcohol solubility, but also polyvinyl alcohol, carboxylic acids, and polyalcohol.

For easier application and better adhesion of the sealed coating it can be useful to create low pressure in the interior of the test tube during the process of wetting. This is best achieved in that a low pressure-generating means (for example a pump) is connected to a closeable suction sleeve which is connected to the tube covering with respect to flow. While wetting the membrane with, for example an inorganic salt, the dissolved salts can penetrate more readily into the pores, and complete sealing of the membrane surface is accomplished sooner.

A particularly diversely applicable arrangement of the test tubes is achieved in that several individual tubes sensitive to different substances are provided whose openings are closed by a common membrane permeable to the substances whose present is to be demonstrated In this way, it becomes possible to test the liquid to be tested simultaneously for several potentially present harmful substances.

A further very simple expedient of a test tube is one in which the sealed membrane is arranged at the end of the tube body provided with a tip which can be broken off. This accomplishes that the test tube is protected during its stand-by time by the still intact tip against a potential gaseous harmful substance. The sealing then only needs to protect during the time between breaking the tip to placing the tube in the liquid and for that reason can be weaker. The delay until indication occurs can, thus, be kept short.

Accordingly, it is an object of the invention to provide a method for testing substances particularly for indicating gases dissolved in liquids using a testing tube which has an opening which exposes the material to be detected which is covered by a membrane which is hydrophobic, but is permeable to the substance to be detected.

A further object of the invention is to provide a tube for detecting substances comprising a tube body with an indicator for the colorimetric indication of substance to be detected arranged in the tube so that there is an opening in the direction of the environment to be investigated and wherein the tube is closed by a hydrophobic membrane which is permeable to the substance to detected and which includes immersing the tip in a liquid to be detected so that a coating which seals the surface of the membrane is dissolved so that the gas which is present permeates through the membrane closing the testing tube through a porous stopper to an indicator in the colorometric material.

A further object of the invention is to provide a testing tube which includes an indicator for the colorimetric indication of substances to be detected arranged in a tube body which has an opening in the direction of the environment to be investigated and which includes a hydrophobic membrane which closes the opening and which is permeable to the substance to be detected.

A further object of the invention is to provide a testing device which is simple in design, rugged in construction and economical to manufacture.

The various features of novelty which characterize the invention are pointed out with particularity in the claims annexed to and forming a part of this disclosure. For a better understanding of the invention, its operating advantages and specific objects obtained by its uses, reference is made to the accompanying drawings and descriptive matter in which preferred embodiments of the invention are illustrated.

GENERAL DESCRIPTION OF THE PREFERRED EMBODIMENTS

Figure 1:
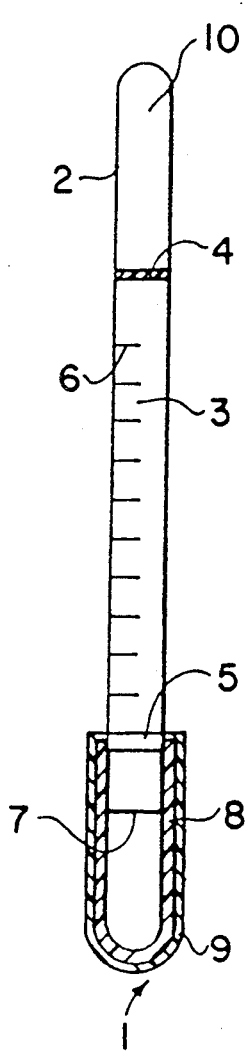
FIG. 1 is a sectional view of a test tube with a sealed membrane in accordance with the invention.

Referring to the drawings, in particular, the invention embodied therein comprises a test tube 2 of a testing device generally designated 1 in which the substance to be detected has an opening to the tube to an indicator 3 therein which is closed by a cap shape membrane 8 which, in the embodiment illustrated, also has an additional coating 9 thereover.

In FIG. 1, a test tube 1 is shown whose tube body 2 is filled with an indicator 3 which is kept between a gas-tight closure 4 and a porous stopper 5. Along the indicator 3 indicator markings 6 are located on the tube body 2. The opening 7 of the test tube 1 to be exposed to the environment to be tested is covered with a cap-shaped membrane 8. The membrane 8 also has a coating 9 for sealing its surface. At the end of the tube body 2 opposite opening 7 is a gas-tight air chamber 10.

After it is immersed in the liquid to be tested, the coating 9 dissolves, the surface of the membrane 8 is freed and the gas whose presence is to be demonstrated permeates through the membrane 8 and the porous stopper 5 into the indicator 3 and leads there to a progressive coloration of the indicator which in a tube body 2 of glass can be directly read on the indicator markings 6.

Figure 2:
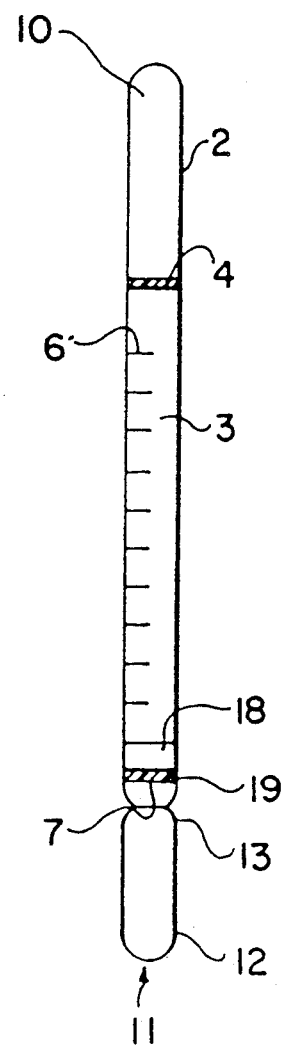
FIG. 2 is a sectional view of another embodiment of a test tube with a tip which can be broken off.

In FIG. 2, an additional embodiment of a test tube 11 is shown whose opening 7 to be exposed to the environment to be tested is covered with a tip 12 which can be broken off at a constriction 13. The permeable membrane is formed in the shape of a permeable stopper 18 and sealed in the direction toward opening 7 with a layer-shaped coating 19. Sealing takes place as long as both tube ends are still open and only stopper 18 alone is inserted. In this state the tip 12 is immersed in the sealed solution while a (not shown) pump is connected to the end at 10 as a suction sleeve. After establishing the sealing the remaining filling of the tube and closing of its two ends takes place.

The remaining details correspond to those of FIG. 1 and are, accordingly, provided with identical reference numbers.

What is claimed is:

1. A tube for testing substances, comprising a tube body, an indicator for the colorimetric indication of substances to be detected arranged in said tube body, said tube body having an opening in the direction of the environment to be investigated, a hydrophobic polymer membrane permeable to the substance to be detected closing the opening, said tube being useable for indicating gases dissolved in liquids and a coating sealing said membrane which is soluble in a liquid.

2. A test tube according to claim 1, wherein said membrane is cup-shaped.

3. A test tube according to claim 1, wherein said membrane comprises a closed tip formation formed at the end of said tube adjacent the opening which is severable to expose the opening.

4. A tube according to claim 1, wherein said coating comprises a lithium chloride.

5. A tube according to claim 1, wherein said coating comprises a copper sulfate.

6. A tube according to claim 1, wherein said tube body is filled at its end opposite to the opening with an air-filled chamber.

7. A tube for testing substances, comprising a tube body, an indicator for the colorimetric indication of substances to be detected arranged in said tube body, said tube body having an opening in the direction of the environment to be investigated, a hydrophobic membrane permeable to the substance to be detected closing the opening, and a liquid-soluble coating comprising a salt sealing said membrane, said tube being useable for indicating gases dissolved in liquids.

8. A method for manufacturing a coating which is used to coat a membrane which is placed over a testing tube containing a colorimetric indicating material comprising wetting a membrane in a hot saturated solution of salt and which thereby forms a property for sealing the test tube and having an addition of a wetting agent in excess, and subsequently evaporating the solvent.

9. A method according to claim 8, wherein during wetting a low pressure is created on the interior of the test tube.

10. A method according to claim 8, wherein the coating is manufactured as a closed additional tip for the testing tube which is connected thereto so as to be breakable away from the testing tube.

* * * * *